(12) United States Patent
Sakagami et al.

(10) Patent No.: US 6,403,864 B1
(45) Date of Patent: Jun. 11, 2002

(54) PRECURSOR POLYPEPTIDE OF A PLANT GROWTH FACTOR, A GENE ENCODING A PRECURSOR POLYPEPTIDE OF A PLANT GROWTH FACTOR AND A METHOD FOR PROMOTION OF PLANT GROWTH

(75) Inventors: Yoji Sakagami; Heping Yang; Yoshikatsu Matsubayashi, all of Nagoya; Kenzo Nakamura, Nisshin, all of (JP)

(73) Assignee: Nagoya University, Nagoya (JP)

( * ) Notice: Subject to any disclaimer, the term of this patent is extended or adjusted under 35 U.S.C. 154(b) by 0 days.

(21) Appl. No.: 09/477,366

(22) Filed: Jan. 4, 2000

(30) Foreign Application Priority Data

Mar. 24, 1999 (JP) .......................................... 11-079612

(51) Int. Cl.⁷ .......................... C12N 5/04; C12N 15/29; C12N 15/82
(52) U.S. Cl. .................... 800/290; 800/278; 800/320.2; 536/23.6; 435/468; 435/419
(58) Field of Search ................................ 800/278, 290, 800/298, 320.2; 536/23.6; 435/410, 419, 468

(56) References Cited

FOREIGN PATENT DOCUMENTS

| EP | 0 821 002 A1 | | 1/1998 |
| WO | 98/21348 | * | 5/1998 |

OTHER PUBLICATIONS

Matsubayashi, Y. et al., "Active Fragments and Analogs of the Plant Growth Factor, Phytosulfokine: Structure–Activity Relationships." 1996, Biochemical and Biophysical Res. Comm., vol. 225, pp. 209–214.*
Bowie, J. et al., "Deciphering the Message in Protein Sequences: Tolerance to Amino Acid Substitutions." 1990, Science, vol. 247, pp. 1306–1310.*
Kato, R. et al., "Effects of an Epidermal Growth Factor on Growth of Zea Primary Roots and Mesocotyls." 1995, Plant Cell Physiol, vol. 36 (1), pp. 197–199.*
Kato, R. et al., "Promotion of Plant Cell Division by an Epidermal Growth Factor." 1993, Plant Cell Physiol, vol. 34 (6), pp. 789–793.*
Yamamoto, K. and Sasaki, T., Accession No. C28090, Aug. 6, 1997.*
Database Genembl 'en ligne!, Aug. 6, 1997, Sasaki, T.: "Rice cDNA partial sequence (C539432A)"; XP002175647; Accession C28090.
Database Genembl 'en ligne!, Aug. 6, 1997, Sasaki, T.: "Rice cDNA partial sequence (C503491A)"; XP002175648; Accession C26886.
Database Genembl 'en ligne!, Aug. 6, 1998 , Sasaki, T.: "Oryza sativa cDNA, partial sequence (C53856—6Z)" XP002175649; Accession C97297.
Database Genembl 'en ligne!, Oct. 7, 1998 , Nakamura, Y.: "Arabidopsis thaliana genomic DNA, chromosone 5, TAC clone:K14B20"; XP002175650; Accession AB018018.
Yang Heping, et al., "Oryza sativa PSK gene 1–6 encodes a precursor of phytosulfokine–alpha, a sulfated peptide growth factor found in plants."; Proceedings of the National Academy of Sciences of the United States, vol. 96, No. 23, Nov. 9, 1999 , pp. 13560–13565; XP002175646; Nov. 9, 1999; ISSN: 0027–8424, National Academy of Sciences, Washington, D.C.
Yang Heping, et al., "A rapid and efficient 4–6 system of Agrobacterium infection–mediated transient gene expression in rice Oc cells and its application for analysis of the expression and antisense suppression of preprophytosulfokine, a precursor of phytosulfokine–alpha, encoded by OsPSK gene."; Plant and Cell Physiology, vol. 41, No. 6, Jun. 2000, pp. 811–816 XP001023456; ISSN: 0032–0781. Oxford University Press, United Kingdom.
Yang Heping, et al., "Molecular cloning and 1–6 characterization of OsPSK, a gene encoding a precursor for phytosulfokine–alpha, required for rice cell proliferation."; Plant Molecular Biology, vol. 44, No. 5, Nov. 2000, pp. 635–647, XP00105809; ISSN: 01647–4412. Kluwer Academic Publishers, Netherlands.
Yang Heping, et al., "Phytosulfokine–alpha, 1–6 a peptide growth factor found in higher plants: Its structure, functions, precursor and receptors." Plant and Cell Physiology, vol. 41, No. 7 Jul. 2000 , pp. 825–830, XP001023457, ISSN: 0032–0781. Oxford University Press, United Kingdom.
"Phytosulfokine, sulfated peptides that induce the proliferation of single mesophyll cells of Asparagus officinalis L", Yoshikatsu Matsubayashi and Youji Sakagami, Proceedings of the National Academy of Sciences of the United States of America, Jul. 23, 1996, vol. 93/No. 15, pp. 7623–7627.

* cited by examiner

Primary Examiner—David T. Fox
Assistant Examiner—Anne Kubelik
(74) Attorney, Agent, or Firm—Burns, Doane, Swecker & Mathis, LLP

(57) ABSTRACT

For the purpose of providing a technique available for the production of a transgenic plant, a method to promote the proliferation of a plant cell is developed. This invention provides an amino acid sequence of precursor polypeptide of phytosulfokine (preprophytosulfokine), a growth factor of plant origin, and a base sequence encoding the phytosulfokine precursor polypeptide. Incorporation of the gene encoding the phytosulfokine precursor polypeptide enables the promotion of plant cell proliferation.

8 Claims, 7 Drawing Sheets

FIG. 1

```
GAAGAAGCAGCAGCAAAAAAGTTGATCAGTTAATTAGCAAGTGTGTTCTTCTTTCTTTTG    60

GTGAGAGAGAGAGAGAGAGAGAGAGAGAGAGAGAGATCTCAGAATGGTGAATCCAGGAAGAA  120
                                         M  V  N  P  G  R   7

CAGCTAGGGCACTCTGCCTCCTATGCCTTGCTCTCCTCCTGCTAGGTCAAGATACCCATT   180
 A  R  A  L  C  L  L  C  L  A  L  L  L  L  G  Q  D  T  H  S    27

CCAGGAAGCTCCTGTTGCAGGAGAAGCACAGCCATGGCGTCGGCAACGGCACAACCACCA   240
 R  K  L  L  Q  E  K  H  S  H  G  V  G  N  G  T  T  T  T       47

CCCAGGAACCAAGCAGAGAGAATGGAGGAAGTACAGGTTCCAATAACAATGGGCAGCTGC   300
 Q  E  P  S  R  E  N  G  G  S  T  G  S  N  N  N  G  Q  L  Q    67

AGTTTGATTCAGCCAAATGGGAAGAATTCCACACGGATTATATCTACACCCAAGATGTCA   360
 F  Ⓓ  S  A  K  W  Ⓔ  Ⓔ  F  H  T  Ⓓ  Y  I  Y  T  Q  Ⓓ  V  K    87
                                     ▲ ══════════ ▲

AAAACCCATAATGGCTGTTCATTTATGATTTGAACTAGTACTAGTAGCTTATACCTTCTG   420
 N  P  *                                                         89

CGCGTCTTTTGTTCGTTTGGAGAGGGGATTTTCTTGGGATTTAGCATATGAACTAATTAA   480

ATTAAATCCCAGGCAAATCCCACTCAGCCCATTTTGTGCAGAAGTTGTCAGTGTGCACTG   540

TATAATTATTTAGTCATACACAACTACTCCTGGTAACTACTCCTATCTTCGATGAATTTT   600

CTGGTTTTGCCAGACGTGACAATAGTCCAGTAGCATGCAGTACCCTCTCAGAATCCCTGT   660

AATTTTTAGCAAAAAAAAAAGGAAGAAAAGAAAAGAAGCTTCCCTACT-Poly(A)       725
```

— — GA repeat sequence

—— N-terminal signal sequence

══ PSK-α sequence

▲ V8 protease recognition site

Ⓞ acidic amino acid

SEQUENCE LISTING

<160> NUMBER OF SEQ ID NOS: 2

<210> SEQ ID NO 1
<211> LENGTH: 89
<212> TYPE: PRT
<213> ORGANISM: Oryza sativa L. Oc cell

<400> SEQUENCE: 1

```
Met Val Asn Pro Gly Arg Thr Ala Arg Ala Leu Cys Leu Leu Cys Leu
 1               5                  10                  15

Ala Leu Leu Leu Gly Gln Asp Thr His Ser Arg Lys Leu Leu Leu
            20                  25                  30

Gln Glu Lys His Ser His Gly Val Gly Asn Gly Thr Thr Thr Thr Gln
        35                  40                  45

Glu Pro Ser Arg Glu Asn Gly Gly Ser Thr Gly Ser Asn Asn Asn Gly
    50                  55                  60

Gln Leu Gln Phe Asp Ser Ala Lys Trp Glu Glu Phe His Thr Asp Tyr
65                  70                  75                  80

Ile Tyr Thr Gln Asp Val Lys Asn Pro
                85
```

<210> SEQ ID NO 2
<211> LENGTH: 725
<212> TYPE: DNA
<213> ORGANISM: Oryza sativa L. Oc cell

<400> SEQUENCE: 2

```
gaagaagcag cagcaaaaaa gttgatcagt taattagcaa gtgtgttctt ctttcttttg    60
gtgagagaga gagagagaga gagagagaga gagatctcag aatggtgaat ccaggaagaa   120
cagctagggc actctgcctc ctatgccttg ctctcctcct gctaggtcaa gatacccatt   180
ccaggaagct cctgttgcag gagaagcaca gccatggcgt cggcaacggc acaaccacca   240
cccaggaacc aagcagagag aatggaggaa gtacaggttc aataacaat gggcagctgc    300 agtttgattc agccaaatgg gaagaattcc acacggatta tatctacacc caagatgtca   360
aaaacccata atggctgttc atttatgatt tgaactagta ctagtagctt ataccttctg   420
cgcgtctttt gttcgtttgg agagggggatt ttcttgggat ttagcatatg aactaattaa   480
attaaatccc aggcaaatcc cactcagccc attttgtgca gaagttgtca gtgtgcactg   540
tataattatt tagtcataca caactactcc tggtaactac tcctatcttc gatgaattt    600 ctggttttgc cagacgtgac aatagtccag tagcatgcag taccctctca gaatccctgt    660 aattttttagc aaaaaaaaaa ggaagaaaag aaaagaagct tccctactaa aaaaaaaaaa    720
aaaaa                                                                725
```

PRECURSOR POLYPEPTIDE OF A PLANT GROWTH FACTOR, A GENE ENCODING A PRECURSOR POLYPEPTIDE OF A PLANT GROWTH FACTOR AND A METHOD FOR PROMOTION OF PLANT GROWTH

BACKGROUND OF THE INVENTION

1. Field of the Invention

This invention relates to an amino acid sequence of a precursor polypeptide of phytosulfokine. Phytosulfokine is a peptide known to enhance proliferation of a plant cell. This invention also relates to a gene encoding said precursor polypeptide. Moreover, this invention relates to a method to promote proliferation of a plant cell by incorporation of said gene into a plant.

2. Description of Related Art

The progression of plant gene engineering techniques has enhanced the production of transgenic plants incorporating various exogenous genes. Such techniques are available for various plant species and play an important role in the development of industry. For example, such techniques enable the production of novel plant species with improved productivity of their secondary metabolites.

For the production of a transgenic plant, it is necessary to cultivate a small number of transformed cells, wherein a certain exogenous gene is incorporated, to regenerate a plant body. However, in the case of a plant cell wherein a certain exogenous gene is incorporated, proliferation of such a cell is very slow. Therefore, regeneration of a plantlet to produce a transgenic plant may be difficult. A plant cell secretes unknown growth factors into the extracellular medium to promote cell division. However, when the plant cells exist in lower density clusters than necessary, proliferation of the plant cells becomes difficult. Often it takes too much time for the growth factor to reach sufficient concentration or the degradation rate of the growth factor exceeds that of secretion. Moreover, in many plant species, cell culture itself is difficult or the rate of cell proliferation is very slow. Therefore, the development of a technique for the promotion of plant cell proliferation has been desired.

SUMMARY OF THE INVENTION

The inventors have purified and isolated phytosulfokine (PSK), as a peptidyl plant growth factor described above (Y. Matsubayashi and Y. Sakagami, Proc. Natl. Acad. Sci. USA 93, p7623, 1996). PSK is one of the plant growth factors contained in so-called "conditioned medium: CM", a medium once used for cell culture. It is known that the PSK is secreted into the extra-cellular medium and functions as an autocrine factor. It is also known that the tyrosine residue of PSK is sulfated by post-translational modification. Two types of PSK, namely PSK-α and PSK-β, are recognized and these sequences are described below. PSK-β is an enzymatic degradation product of PSK-α and the cell proliferation activity observed in PSK-β is less than one-tenth of that of PSK-α.

PSK-α: Tyr($SO_3H$)-Ile-Tyr($SO_3H$)-Thr-Gln

PSK-β: Tyr($SO_3H$)-Ile-Tyr($SO_3H$)-Thr

The existence of a physiologically active plant peptide or protein in which the tyrosine residue is sulfated was not known until the discovery of PSK. In animals, about 30 species, including cholecystokinin or gastrin, are known to exhibit such a property. They are all extra-cellularly secreted peptides bio-synthesized as their precursors, sulfated and processed during transition via the trans-Golgi network. It is assumed that excision of the PSK sequence occurs in the same manner. The presence of a certain signal sequence is predicted in the precursor peptides wherein their tyrosine residue is specifically sulfated, as the precursor peptides are secreted into the extra-cellular region. Concerning the PSK peptide, the existence of a precursor peptide is predicted based on such knowledge. Therefore, the gene encoding the precursor polypeptide of rice PSK was isolated and the base sequence of the precursor gene was determined. The gene thus obtained was incorporated into rice Oc culture cells, and the effect of the gene was investigated. The over-expression of the gene encoding the PSK precursor polypeptide increased the secretion of PSK into cultured medium and promoted the proliferation of rice Oc cells.

The precursor polypeptide of PSK (preprophytosulfokine) of this invention is identified by an amino acid sequence referred to as SEQ ID NO: 1. The gene encoding preprophytosulfokine is identified by a base sequence referred to as SEQ ID NO: 2.

In general, one amino acid is encoded by a plurality of base sequences of DNA. Therefore, a plurality of genes, other than native gene of this invention, might encode amino acid sequences identical to preprophytosulfokine. The gene of this invention is not to be limited to only the native gene and is intended to include many other base sequences encoding preprophytosulfokine.

The precursor polypeptide of PSK of this invention includes a polypeptide having an amino acid sequence at least 40% sequence homology to the amino acid sequence of SEQ ID NO: 1, while retaining the biochemical characteristics of preprophytosulfokine. In a preferred form, the precursor polypeptide of this invention has more than 50% sequence homology to the amino acid sequence of SEQ ID NO: 1. In a more preferred form, the precursor polypeptide of this invention has more than 80% sequence homology to the amino acid sequence of SEQ ID NO: 1.

Moreover, the gene of this invention includes a gene that encodes the precursor polypeptide of PSK described above consisting of a base sequence that hybridizes with the base sequence of SEQ ID NO: 2 under stringent conditions.

The proliferation of a plant cell can be promoted by the incorporation of a gene encoding preprophytosulfokine. A plant cell, wherein a certain exogenous gene is incorporated, tends to decrease its proliferation rate. Especially, this technique enhances the proliferation of said cell with a decreased proliferation rate. Therefore, cell differentiation and regeneration of a plantlet would be achieved by incorporation of the gene encoding preprophytosulfokine. Moreover, growth enhancement of a plant would be achieved by incorporation of the gene. The gene disclosed in this invention can be incorporated into various plants. The plants described below are plants preferable for incorporation of the gene. These are monocotyl plants such as rice, maize, asparagus and wheat or dicotyl plants such as arabidopsis, tobacco, carrot, soy bean, tomato and potato. For a technique to produce a transformant, ordinary techniques known in the art can be adopted. For an example of an available vector, pAct-nos/Hmz can be mentioned. Such a vector can be introduced into Agrobacterium, for example, and a transformant can be produced by infection of a callus or an infant plant. The Examples described above and the embodiments described below are preferred embodiments of this invention and do not intend to exhibit the limits or the range of this invention.

These and other objects and advantages of the invention will become more apparent upon a reading of the detailed description and drawings.

BRIEF DESCRIPTION OF THE DRAWINGS

FIG. 1 is a figure showing a base sequence and an amino acid sequence of the OsPSK gene.

DETAILED DESCRIPTION OF THE PREFERRED EMBODIMENTS

Cloning of PSK-α

Figure 2:
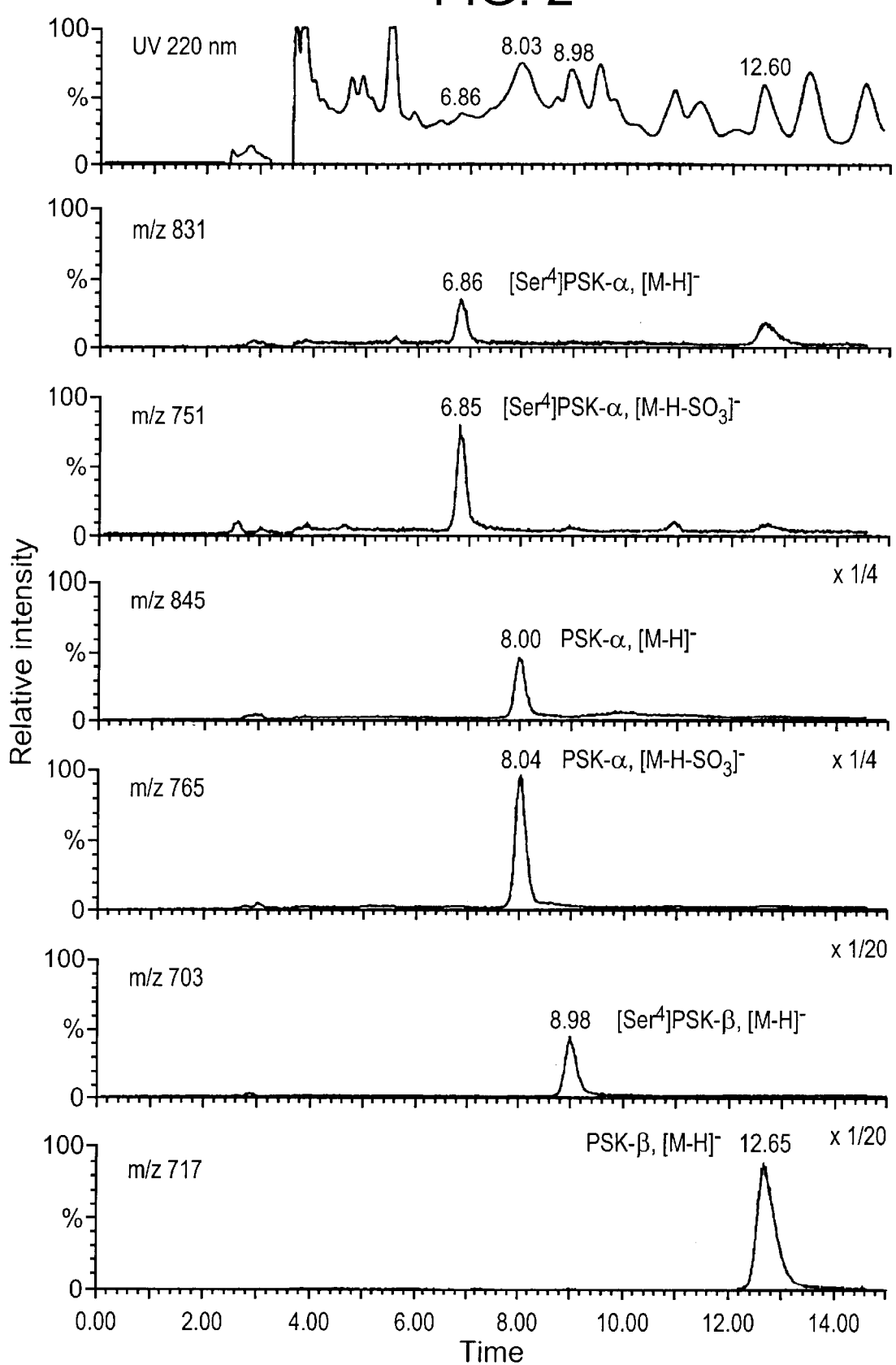
FIG. 2 is a figure showing the detection of PSK analogs existing in conditioned medium of transformed rice Oc cells, using LC-MS spectrometry.

Screening was performed as described below, on a cDNA library constructed from rice Oc cells with mixed degenerate oligonucleotides corresponding to amino acid sequences of PSK-α. Poly (A)+RNA was purified with oligo (dT) columns from Oc cells cultured for 10 days. A cDNA library was constructed with ZAP-cDNA Synthesis Kit (Stratagene, La Jolla, Calif.). Ninety-six kinds of 15-mer oligonucleotides corresponding to amino acid sequences of PSK-α were synthesized, labeled by [γ-$^{32}$p] ATP with a Kination Kit (Toyobo, Osaka), and used for the screening of the cDNA library by plaque hybridization at 25° C. in a solution containing 6×saline sodium citrate (SSC), 20 mM NaH$_2$PO$_4$, 0.4% SDS, 5×Denhardt's solution, and 500 μg/l salmon sperm DNA. Filters were washed in several changes of 6×SSC and 0.1% SDS at 25° C. for 1 hour. As a result, three cDNA clones hybridized with the probes.

The pBluescript plasmids containing the positive inserts were excised and introduced into *Escherichia coli* strain SOLR. The subcloned inserts were sequenced using BigDye Terminator Cycle Sequencing Kit and ABI PRISM 310 Genetic Analyzer (Applied Biosystems, Foster, Calif.) in accordance with the manufacturer's protocols. The result showed that, one cDNA clone encodes the precursor of phytosulfokine. The cDNA thus obtained is designated as OsPSK.

The Structure and Features of the PSK Precursor Polypeptide and the Gene Encoding the Precursor Polypeptide The result of sequence analysis revealed that the OsPSK cDNA was 725 base pairs (bp) in length. The base sequence of the OsPSK cDNA is shown in the upper sequence of FIG. 1 and SEQ ID NO: 2. The sequence contained sixteen GA repeats in the 5'-untranslated region (FIG. 1 dotted line). The open reading frame was 267 bp long encoding preprophytosulfokine (precursor of the PSK polypeptide), consisting of 89 amino acids. The amino acid sequence of preprophytosulfokine is shown in the lower sequence of FIG. 1 and as SEQ ID NO: 1. The sequence of FIG. 1 suggested a predicted molecular mass of 9.8 kD and an isoelectric point of 6.48. A 22-amino acid hydrophobic region that resembled a cleavable leader peptide was found at the NH$_2$-terminus of the preprophytosulfokine. Such hydrophobic region structure is found in animal bioactive peptide precursors. The predicted mature form of preprophytosulfokine contains a high percentage of charged amino acids (6% aspartic acid, 7.5% glutamic acid, and 6% lysine) and is therefore hydrophilic. Of the 89-amino acid preprophytosulfokine, amino acids 80 through 84 encode PSK-α (FIG. 1 double line).

Sulfated tyrosines are usually located within acidic regions of secretory proteins. All sites which have been characterized in animals have aspartic and glutamic residues near the sulfated tyrosine. The acidic amino acids are shown by circles in FIG. 1. There is an aspartic acid residue immediately NH$_2$-terminal to the first tyrosine of PSK-α in the −1 position, and two or three acidic residues are found between −5 and +5 around the first or second tyrosine residue in PSK-α, respectively. Such features in the structure suggest that the tyrosine residues could be sulfated by sulfotransferase. The putative processing sites bordering PSK conformed to the consensus sequence for V8-peptidase, suggesting that PSK could be proteolytically processed from preprophytosulfokine. The V8-peptidase recognition sites are indicated by arrows. No significant homology was found between the cDNA and other sequences in the DNA data banks, except for several expressed sequence tags from rice with no known function.

Transformation by Incorporation of the OsPSK Gene

To confirm that the OsPSK gene is indeed coding for PSK-α, rice Oc cells were transformed with a mutated cDNA of OsPSK. The mutated cDNAs used for the transformation are designed to produce mutated PSK-α or PSK-β wherein threonine, located at the fourth position of the peptides, is substituted by serine. The serine-substituted PSK-α is termed [Ser$^4$]PSK-α and the serine substituted PSK-β is termed [Ser$^4$]PSK-β, respectively. The sequences of [Ser$^4$]PSK-α and [Ser4]PSK-β are described below.

[Ser$^4$]PSK-α: Y(SO$_3$H)IY(SO$_3$H)SQ

[Ser$^4$]PSK-β: Y(SO$_3$H)IY(SO$_3$H)S

A 22-mer primer (5'-CATCTTGGGAGTAGATATAATC-3') was synthesized and used to obtain mutated preprophytosulfokine cDNA described above with an in vitro mutagenesis kit(Takara, Tokyo). The pAct-nos/Hmz vector harboring kanamycin and hygromycin resistance genes for transformant selection was employed as a binary vector for Oc cell transformation. The wild type or serine-mutated cDNA was excised with Sma I and Eco RV and inserted into the Sma I site of the vector. Expression of the chimeric genes was driven by the rice actin promoter incorporated within the binary vector. The constructs were transformed into Agrobactereium strain LBA4404 by triparental mating and the Agrobacterium-mediated transformation of Oc cells was performed.

Measurement of PSK-α and its Analogs

The amounts of PSK-α and its analogs, released into medium by wild type strain or transformant, was measured by liquid chromatography/ mass spectrometry (LC-MS) analysis. Conditioned medium (CM) derived from 14-day cultured wild or transformed Oc cells was chromatographed on DEAE Sephadex A-25 column. PSK-α and PSK-β contained in 800 and 1,200 mM KCl fractions were adsorbed on Sep-Pak Vac Cartridges, eluted with 30% acetonitrile containing 0.1 % trifluoroacetic acid, and lyophilized. Mass spectra were obtained using a Fisons VG platform quadruple mass spectrometer with electrospray ionization interfaced to a Jasco PU980 HPLC system. The fractions containing PSKs were dissolved in 200 µl of water and separated on a reverse-phase HPLC column (4.6×250 mm) with 10% acetonitrile containing 0.1% trifluoroacetic acid at 1.0 ml/min. The pseudomolecular ions of PSKs were monitored by scanning every 1.9 s in the selective ion monitoring mode. Amino acid sequences of the peptides were determined by Applied Biosystems model 490 sequencer.

The Effect of OsPSK Gene Incorporation on Secretion of PSK Analogs

The result of quantitative analysis of PSK analogs performed by LC-MS, as described above, is shown in FIG. 2. In FIG. 2 peaks corresponding to [Ser$^4$]PSK-α (retention time 6.9 min), PSK-α (retention time 8.0 min), [Ser$^4$]PSK-β (retention time 9.0 min) and PSK-β (retention time 12.7 min) were detected in the elution derived from CM of the transgenic Oc cells with the mutated cDNA. Furthermore, the peptides contained in the corresponding fractions were sequenced and confirmed that they indeed were [Ser$^4$] PSK-α and -β, respectively, supporting the hypotheses that OsPSK cDNA encodes preprophytosulfokine and that PSK-β is an enzymatic degradation product of PSK-α.

Furthermore, OsPSK cDNA was introduced in sense and antisense orientation into Oc cells using the same binary vector. Then the amounts of PSK-α and -β were analyzed by LC-MS. The control or transformed Oc cells (0.8 g) were planted in 100 ml of fresh medium, and the amounts of PSK-α and its analogs were analyzed after one week cultivation. The results indicated by the average values of three independent experiments with standard deviations were shown in Table 1 (unit of concentration: nM). PSK-α and -β accumulated in the CM of the sense transformant were 1.6 times as concentrated as in the control. The increase of PSK secretion was proven to be caused by introduction of the gene. The amounts of PSK-α and -β accumulated in the antisense transformant CM were less than 60% of the mean control level, indicating decrease of PSK secretion. On the other hand, the total amount of [Ser$^4$]PSK-α and -β was only about 34% of the wild type PSK-α and -β, suggesting that the amino acid replacement may decrease processing and/or modification efficiency.

TABLE 1

Accumulation of PSKs in media conditioned by control or transgenic Oc cells

| Cell Type | PSK-α | PSK-β | [Ser$^4$]PSK-α | [Ser$^4$]PSK-β |
|---|---|---|---|---|
| Control | 12.6 ± 1.1 | 332.7 ± 20.1 | 0 | 0 |
| Antisense | 7.3 ± 0.4 | 175.8 ± 15.4 | 0 | 0 |
| Sense | 21.0 ± 1.9 | 555.7 ± 31.1 | 0 | 0 |
| [Ser$^4$]mutant | 11.5 ± 0.9 | 302.5 ± 15.8 | 3.1 ± 0.3 | 105.2 ± 8.9 |

The Effect of OsPSK on Cell Proliferation

Figure 3:
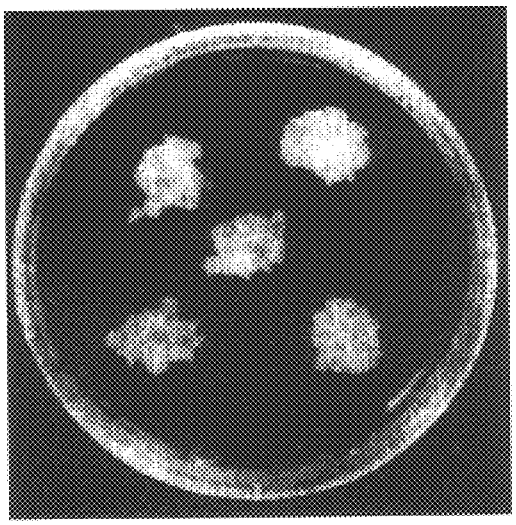
FIG. 3 is a picture of non-transformed rice Oc cells after two weeks of cultivation.
Figure 4:
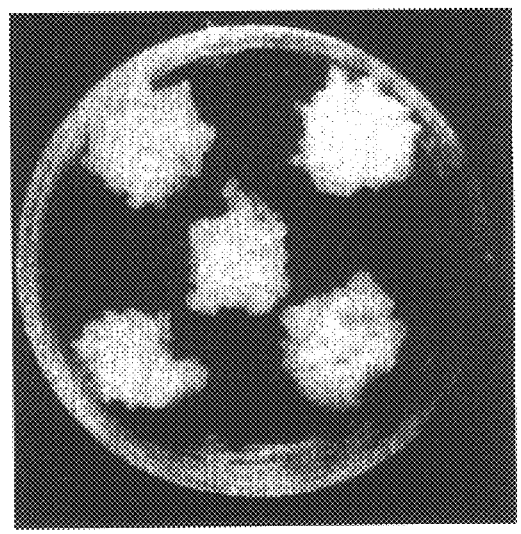
FIG. 4 is a picture of rice Oc cells wherein the OsPSK gene is incorporated in sense orientation, after two weeks of cultivation.
Figure 5:
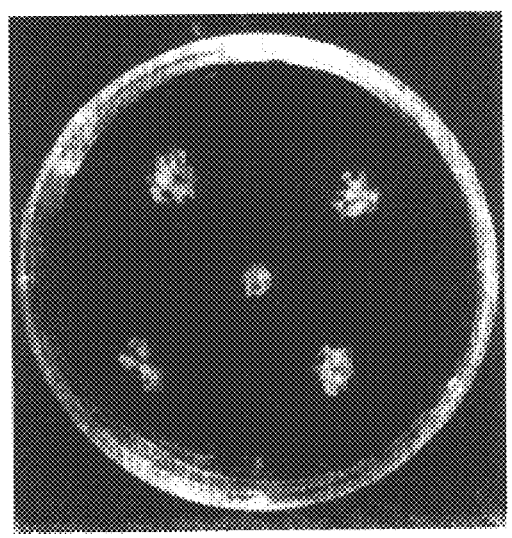
FIG. 5 is a picture of rice Oc cells wherein the OsPSK gene is incorporated in anti-sense orientation, after two weeks of cultivation.

The effects of the OsPSK gene on cell proliferation were investigated. The result showed that, the S2 sense transgenic cells divided about two times faster (FIG. 4) than the control (FIG. 3), while the A2 antisense transformants slowed their cell mitogenic activities (FIG. 5). Moreover, supplying the antisense transformants with PSK-α recovered their mitogenic activities in part (38~64%), indicating that the OsPSK gene promotes plant cell division.

Figure 6:
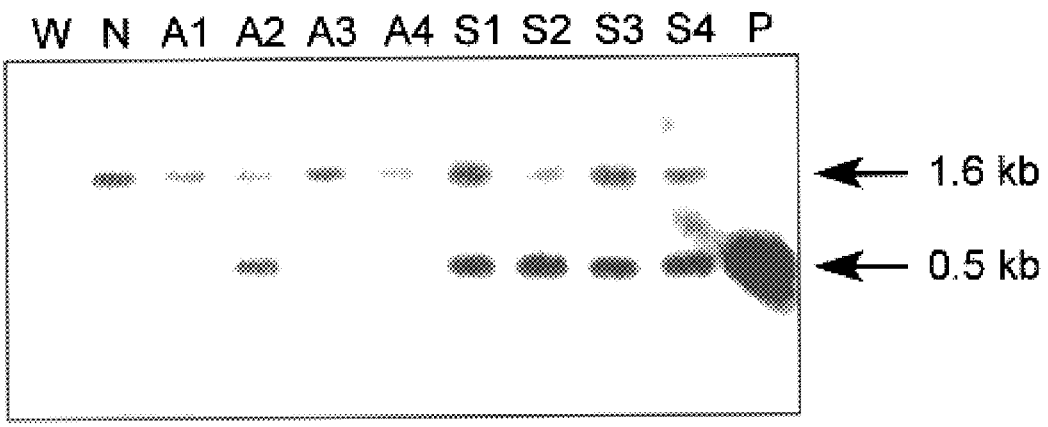
FIG. 6 is a picture of a blotting showing the detection of the OsPSK gene in rice Oc cells wherein said gene is incorporated in sense and anti-sense orientations.

Then the existence of incorporated gene in the transformed cells was confirmed by southern blotting (FIG. 6). In FIG. 6, each lane indicates the following samples.

W: Water only

N: Non-transformed rice Oc cells

A1–A4: Anti-sense transformed cells

S1 –S4: Sense transformed cells

P: Expression vector only

In FIG. 6, a band of 0.5 kb corresponding to the incorporated OsPSK gene was recognized in the S1–S4 sense transformed cells and the A2 anti-sense transformed cells. The band of 1.6 kb corresponding to the endogenous OsR-Acl gene was observed in both the sense transformed cells and the anti-sense transformed cells.

The Features of Expression of the OsPSK Gene

Figure 7:
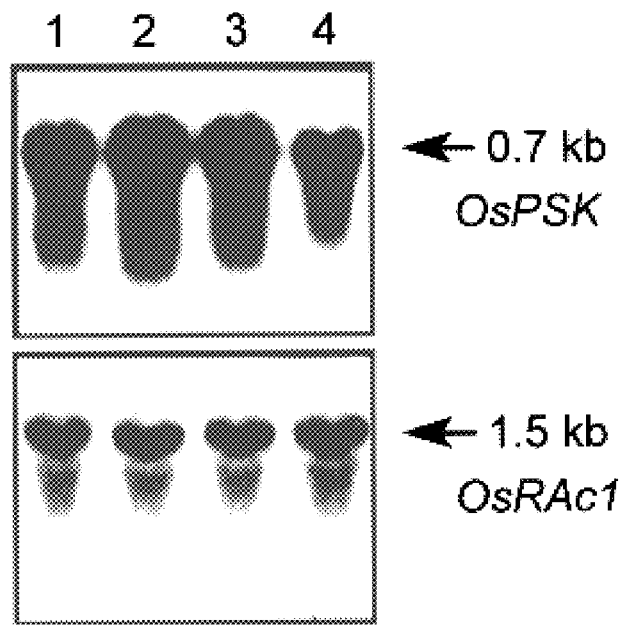
FIG. 7 is a picture of a blotting showing the expression of the OsPSK gene in rice Oc cells, at 3, 7, 10 and 14 days after transplanting.
Figure 8:
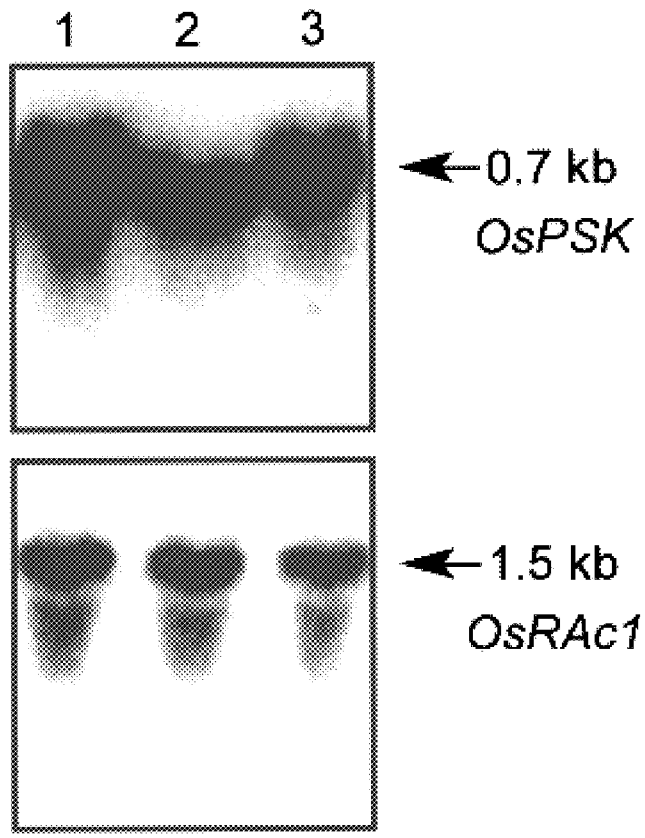
FIG. 8 is a picture of a blotting showing the expression of the OsPSK gene in rice Oc cells wherein said gene is incorporated in sense and anti-sense orientations.
Figure 9:
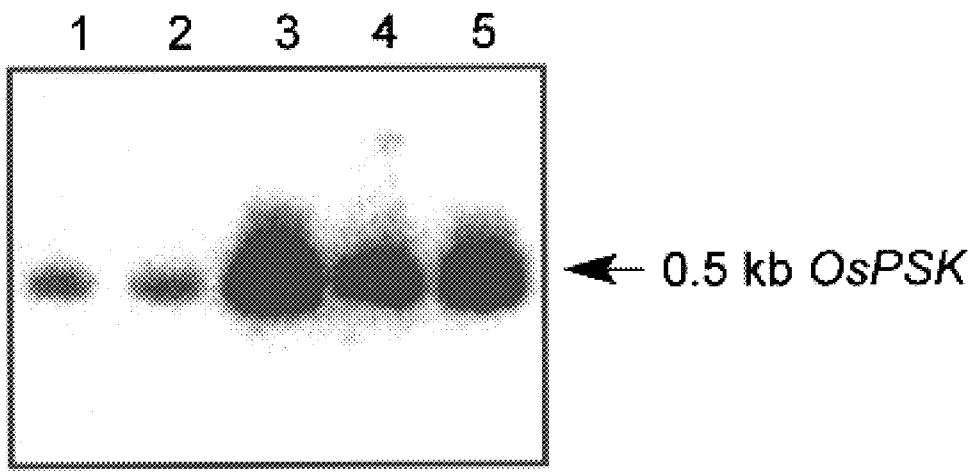
FIG. 9 is a picture of a blotting showing the expression of the OsPSK gene in rice seedlings, investigated on various portions of the plant body.

The alteration of expression of the OsPSK gene that accompanied different times of the culture period was analyzed by northern blot analysis performed by hybridization with labeled full-length cDNA at 60° C. In FIG. 7, the results in lane 1, lane 2, lane 3, and lane 4 indicate the results of 3 days, 7 days, 10 days, and 14 days after transplanting, respectively. The results in FIG. 7 revealed that the OsPSK gene was continuously expressed in Oc culture cells providing a continuous supply of PSK and allowing the cells to proliferate rapidly. Especially, the OsPSK gene was expressed most abundantly 10 to 14 days after transplanting. The expression of the OsPSK gene in the transformed cells was confirmed in FIG. 8. The expression of the OsPSK gene in sense transformed cells of lane 1 increased compared to that of non-transformed cells (lane 3). On the other hand, that in antisense transformed cells decreased (lane 2). Moreover, the expression pattern in rice seedlings was investigated (FIG. 9). The pattern shown in lane 1, lane 2, lane 3, lane 4, and lane 5 indicates the results of the first leaf, the second leaf, shoot tip, lateral root, and seminal root, respectively. Significant expression of the gene in the shoot tip and the seminal root and lesser expression in the leaves are shown in FIG. 9. These results indicate that regions with active growth exhibit abundant expression of the OsPSK gene.

Finally, Southern blot analysis was performed after treatment with various restriction enzymes. The restriction enzymes used for the enzyme treatment of FIG. 10 were Bam HI (Ba), Eco RI (Ec), Xba I (Xb), and Xho I (Xh). Multiple bands were observed in the Eco RI treated sample, suggesting that the OsPSK gene might belong to a small multigene family. However, the multiple hybridizing bands derived from Eco RI digestion could be attributed to the restriction sites found in OsPSK cDNA. To verify this notion, another blot was done using a 300 base pair-fragment from the 5' terminal of OsPSK cDNA. As expected, only one band (3.7 kilobase pair) was apparent by hybridization. Therefore, it seems that preprophytosulfokine is encoded by a single gene, not by a multigene family.

Figure 10:
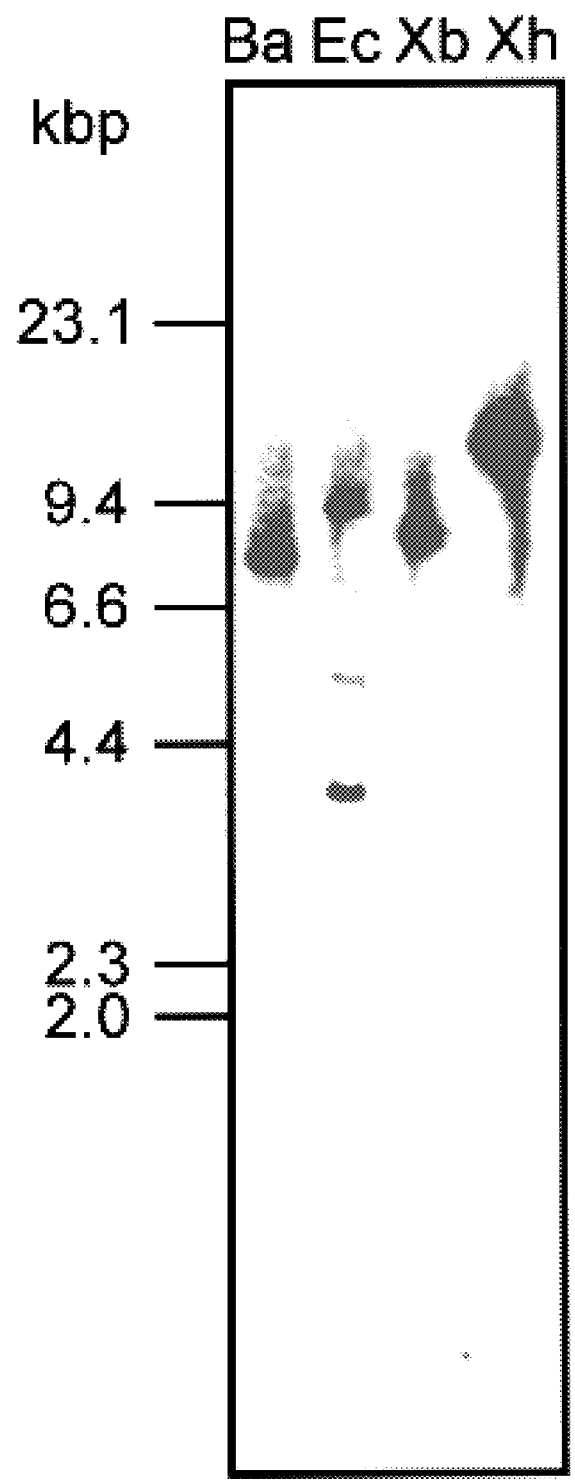
FIG. 10 is a picture of a blotting showing the copy numbers of the OsPSK gene, investigated after treatment with various restriction enzymes.
Figure 11:
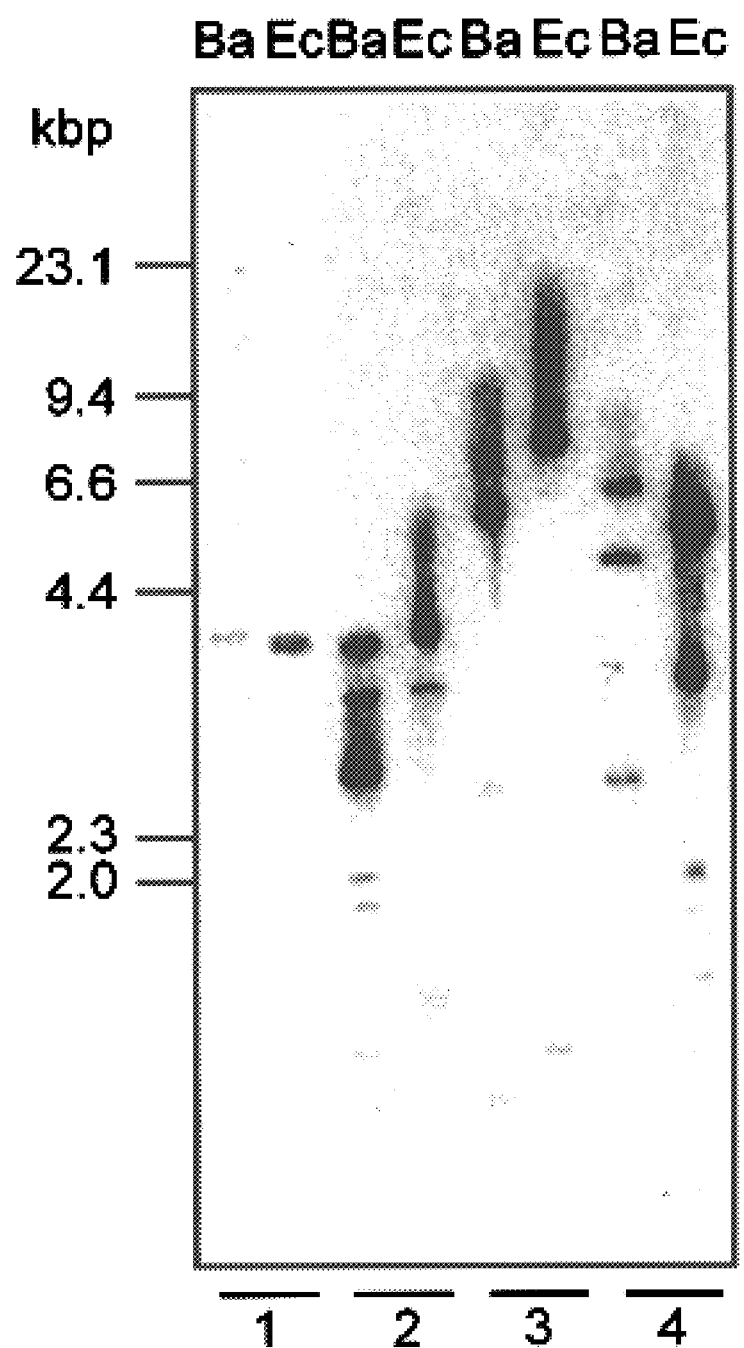
FIG. 11 is a picture of a blotting showing the conservation of the OsPSK gene investigated in *Arabidopsis thaliana, Asparagus officinalis, Daucus carota*, and *Zinnia elegans*.

To determine if OsPSK homologs are found in other plant species, Southern blot analysis was performed after restriction enzyme treatment as described in FIG. 10. Enzyme treatments of FIG. 11 were Bam HI (Ba) and Eco RI (Ec), respectively. Southern blot analysis was performed on genomic DNA from four species known to produce PSK, *Arabidopsis thaliana* (column 1), *Asparagus officinalis* (column 2), *Daucus carota* (column 3), and *Zinnia elegans* (column 4). OsPSK homologs were detected in all four species as shown in FIG. 11, suggesting that the OsPSK gene is conserved in both monocots and dicots. Therefore, it is assumed that, incorporation of the OsPSK gene is effective in various species of plants.

The amino acid sequence of the precursor polypeptide of phytosulfokine (preprophytosulfokine), a growth factor of plant origin, and the base sequence encoding said precursor polypeptide were provided by this invention. The incorporation of said gene into rice Oc cells resulted in increased secretion of phytosulfokine into medium and promotion of cell growth.

What is claimed is:

1. A purified DNA encoding a precursor polypeptide of phytosulfokine, wherein said precursor polypeptide comprises
   amino acids 1 to 89 in SEQ ID NO: 1.

2. A purified DNA according to claim 1, wherein said DNA comprises
   bases 1 to 725 in SEQ ID NO: 2.

3. A plant cell comprising a construct comprising the DNA of claim 2.

4. A method to promote proliferation of a rice cell, comprising incorporating the DNA according to claim 2 into said rice cell, thereby promoting proliferation of said cell.

5. A plant cell comprising a construct comprising the DNA of claim 1.

6. A method to promote growth of a rice cell, comprising incorporating of the DNA according to claim 2 into said rice cell, thereby promoting growth of said rice cell.

7. A method to promote proliferation of a rice cell, comprising incorporating the DNA according to claim 1 into said rice cell, thereby promoting proliferation of said cell.

8. A method to promote growth of a rice cell, comprising incorporating of the DNA according to claim 1 into said rice cell, thereby promoting growth of said rice cell.

* * * * *